United States Patent [19]
Timmons et al.

[11] Patent Number: 6,110,487
[45] Date of Patent: Aug. 29, 2000

[54] METHOD OF MAKING POROUS KERATIN SCAFFOLDS AND PRODUCTS OF SAME

[75] Inventors: Scott F. Timmons; Cheryl R. Blanchard, both of San Antonio, Tex.; Robert A. Smith, Jackson, Miss.

[73] Assignee: Keraplast Technologies Ltd., San Antonio, Tex.

[21] Appl. No.: 09/198,998

[22] Filed: Nov. 24, 1998

Related U.S. Application Data

[63] Continuation-in-part of application No. 08/979,526, Nov. 26, 1997, and a continuation of application No. 09/057,161, Apr. 8, 1998, and a continuation of application No. 08/979,456, Nov. 26, 1997.

[51] Int. Cl.[7] .............................. A61K 9/70; A61K 9/00; A61K 38/00; A61K 38/17; C08G 63/48
[52] U.S. Cl. ........................... 424/443; 424/400; 514/21; 525/54.1; 530/357
[58] Field of Search .................................... 424/400, 443; 514/21; 530/357; 525/54.1

[56] References Cited

U.S. PATENT DOCUMENTS

| | | | |
|---|---|---|---|
| 2,993,794 | 7/1961 | Moshy | 99/18 |
| 4,135,942 | 1/1979 | Kikkawa | 106/155 |
| 4,141,888 | 2/1979 | Matsuda et al. | 260/123.7 |
| 4,570,629 | 2/1986 | Widra | 128/156 |
| 4,983,580 | 1/1991 | Gibson | 514/2 |
| 5,258,043 | 11/1993 | Stone | 623/66 |
| 5,276,138 | 1/1994 | Yamada et al. | 530/357 |
| 5,358,935 | 10/1994 | Smith et al. | 514/21 |
| 5,487,889 | 1/1996 | Eckert et al. | 424/93.1 |
| 5,712,252 | 1/1998 | Smith | 514/21 |
| 5,763,583 | 6/1998 | Arai et al. | 530/353 |

FOREIGN PATENT DOCUMENTS

| | | |
|---|---|---|
| 6-100600 | 4/1994 | Japan . |
| 531446 | 1/1941 | United Kingdom . |

*Primary Examiner*—Shelley A. Dodson
*Assistant Examiner*—Marina Lamm
*Attorney, Agent, or Firm*—Crompton, Seager & Tufte, LLC

[57] ABSTRACT

Methods for producing thin keratin films, sheets, and bulk materials, and products formed using these methods. One method includes providing hair, reducing the hair such that the disulfide linkages are broken and free cysteine thiol groups formed, separating out a more soluble keratin fraction in solution, forming a thin layer from the more soluble fraction, and air drying the keratin fraction in the presence of oxygen, thereby forming new disulfide bonds imparting strength to the resulting thin keratin film. One method includes reducing hair by heating the hair under nitrogen in an ammonium hydroxide and ammonium thioglycolate solution followed by centrifuging and collecting the supernatant containing the more soluble keratin fraction. The more soluble keratin in this method is precipitated using HCl, removed, and resuspended in ammonium hydroxide. The keratin solution thus formed is poured onto a flat surface and allowed to air dry into a thin keratin film. The film may be used as a wound dressing, a tissue-engineering scaffold, a diffusion membrane, a coating for implantable devices, and as a cell encapsulant. In another method, the keratin solution thus formed is concentrated, poured into a mold, and allowed to air dry into a three dimensional keratin product. The resulting bulk product can be used as a cross-linked implantable biomaterial for soft and hard tissue replacement. In another method, a keratin solution is emulsified and freeze dried, forming a porous, open cell keratin material.

20 Claims, No Drawings

METHOD OF MAKING POROUS KERATIN SCAFFOLDS AND PRODUCTS OF SAME

CROSS REFERENCE TO RELATED APPLICATIONS

The present application is a continuation-in-part of U.S. patent application Ser. No. 08/979,526, filed Nov. 26, 1997, entitled KERATIN-BASED SHEET MATERIAL FOR BIOMEDICAL APPLICATIONS AND METHOD OF PRODUCTION. The present application is continuation of to U.S. patent application Ser. No. 09/057,161, filed Apr. 8, 1998, entitled KERATINOUS PROTEIN MATERIAL FOR WOUND HEALING APPLICATIONS; U.S. patent application Ser. No. 08/979,456, filed Nov. 26, 1997, entitled KERATIN-BASED HYDROGEL FOR BIOMEDICAL APPLICATIONS AND METHOD OF PRODUCTION; and U.S. Pat. No. 5,358,935, entitled NONANTIGENIC KERATINOUS PROTEIN MATERIAL, all herein incorporated by reference.

FIELD OF THE INVENTION

The present invention is related to products formed from Keratin derived from hair. More specifically, the present invention is related to films, sheets, and bulk materials formed from keratin. The present invention is directed to a cross-linked keratin based bulk, film or sheet material for use in biomedical implant, wound dressing, and tissue engineering applications. More specifically, one aspect of the present invention relates to a material based primarily on alpha keratin produced by cross-linking keratin derived from a soluble fraction of keratinous material such as hair.

BACKGROUND OF THE INVENTION

Chronic wounds can be caused by a variety of events, including surgery, prolonged bed rest, and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers), and venous stasis disease, which can cause full thickness ulcers of the lower extremities. Full thickness wounds tend to heal very slowly. Proper wound care technique, including the use of wound dressings, is extremely important to successful chronic wound management. Chronic wounds affect an estimated four million people a year, resulting in health care costs in the billions of dollars. "Treatment of Skin Ulcers with Cultivated Epidermal Allografts," T. Phillips, O. Kehinde, and H. Green, *J. Am. Acad. Dermatol.*, V. 21, pp. 191–199 (1989).

The wound healing process involves a complex series of biological interactions at the cellular level, which can be grouped into three phases: hemostasis and inflammation, granulation tissue formation and reepithelization; and remodeling. "Cutaneous Tissue Repair: Basic Biological Considerations," R. A. F. Clark, *J. Am. Acad. Dermatol.*, Vol. 13, pp. 701–725 (1985). Keratinocytes (epidermal cells that manufacture and contain keratin) migrate from wound edges to cover the wound. Growth factors such as transforming growth factor-β (TGF-β) play a critical role in stimulating the migration process. The migration occurs optimally under the cover of a moist layer. Keratins have been found to be necessary for reepithelization. Specifically, keratin types K5 and K14 have been found in the lower, generating, epidermal cells, and types K1 and K10 have been found in the upper, differentiated cells. Wound Healing: Biochemical and Clinical Aspects, I. K. Cohen, R. F. Diegleman, and W. J. Lindblad, eds., W.W. Saunders Company, 1992. Keratin types K6 and K10 are believed to be present in healing wounds, but not in normal skin. Keratins are major structural proteins of all epithelial cell types and appear to play a major role in wound healing.

An optimum wound dressing would protect the injured tissue, maintain a moist environment, be water permeable, maintain microbial control, deliver healing agents to the wound site, be easy to apply, not require frequent changes, and be non-toxic and non-antigenic. Although not ideal for chronic wounds, several wound dressings are currently on the market, including occlusive dressings, non-adherent dressings, absorbent dressings, and dressings in the form of sheets, foams, powders, and gels. Wound Management and Dressing, S. Thomas, The Pharmaceutical Press, London, 1990.

Attempts have been made to provide improved dressings that would assist in the wound healing process using biological materials such as growth factors. To date, these biologicals have proven very costly and have shown minimal clinical relevance in accelerating the chronic wound healing process. In cases of severe full thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water-permeable layer, but is rejected by the patient usually within two weeks and does not become part of the new epidermis.

What would be desirable, and has not heretofore been provided, is a wound dressing that protects the injured tissue, maintains a moist environment, is water permeable, is easy to apply, does not require frequent changes, is non-toxic and non-antigenic, and most important, delivers effective healing agents to the wound site.

Film materials compatible with living tissue are useful for a number of applications including tissue engineering scaffolding, diffusion membranes, coatings for implantable devices, and cell encapsulants. Bulk keratin materials compatible with living tissue are useful for a number of applications including open cell tissue engineering scaffolding and bulk, cross-linked biomaterials. Tissue engineering is a rapidly growing field encompassing a number of technologies aimed at replacing or restoring tissue and organ function. The consistent success of a tissue-engineered implant rests on the invention of a biocompatible, mitogenic material that can successfully support cell growth and differentiation and integrate into existing tissue. Such a scaffolding material could greatly advance the state of the tissue engineering technologies and result in a wide array of tissue engineered implants containing cellular components, such as osteoblasts, chondrocytes, keratinocytes, and hepatocytes, to restore or replace bone, cartilage, skin, and liver tissue respectively.

Diffusion membranes are commonly formed of synthetic polymeric materials, rather than biologically-derived materials. Diffusion membranes derived from biological materials have the advantage of enhanced biocompatibility. In particular, non-antigenic diffusion membranes are compatible with implantation in the human body and would provide great advantages in controlled drug release applications.

Implantable devices, such as pacemakers, stents, orthopedic implants, urological implants, dental implants, breast implants, and implants for maxillofacial reconstruction are currently encased in, or made of, materials including titanium, silicone, stainless steel, hydroxyapatite, and polyethylene, or encapsulated in materials such as silicone or polyurethane. These metals, ceramics, and synthetic polymers have disadvantages related to biocompatibility and antigenicity which can lead to problems related to the long term use of these devices. A coating material derived from biological materials and having non-antigenic and mitogenic properties would provide a device the advantage of long term biocompatibility in vivo and potentially extend the useful lifetime of an implant while decreasing the risk of an allergic or negative immune response from the host.

Cell encapsulants such as Chitin/Alginate and bovine-derived collagen are used to encapsulate mammalian cells for applications such as tissue engineering/organ regeneration and bacteria for cloning applications. A non-antigenic, non bioresorbable cell encapsulant material would have the advantages of providing the cell with a mitogen and increasing the chances for the cell to accomplish its tissue engineering function.

A bulk, cross-linked implantable biomaterial that was non-antigenic and possessed the appropriate mechanical properties could be used for maxillofacial restoration, for example, for both soft and hard tissue replacement. Such a bulk material could also be used for orthopedic applications as a bone filler and for cartilage regeneration. A bulk material capable of being implanted could also be used for neurological applications, such as for nerve regeneration guides.

Keratin, often derived from vertebrate hair, has been processed into various forms. Commonly assigned U.S. Pat. No. 5,358,935 discloses mechanically processing human hair into a keratinous powder. The hair is bleached, rinsed, dried, chopped, homogenized, ultrasonicated, and removed from solvent, leaving a keratin powder. In U.S. Pat. No. 5,047,249, Rothman discusses activating keratin with a reducing agent and applying the activated keratin to a wound. Rothman believes the activated keratin thiol groups will react with thiol groups in the wound tissue and form a disulfide bond, allowing the keratin to adhere to and protect the wound.

Keratin derived materials are believed to be non-antigenic, particularly when derived from a patient's own keratin. A film formed from keratin based material would be desirable. A keratin film able to be used for tissue-engineering scaffolds, diffusion membranes, implantable device coatings, and cell encapsulants would be very useful. A solid keratin bulk material would also have great utility. In addition, a non-antigenic, mitogenic open cell keratin scaffold would prove highly beneficial for use as a tissue engineered scaffold to support, nourish, and stimulate cell growth preceding and following implantation.

SUMMARY OF THE INVENTION

The present invention includes a sheet formed of cross-linked keratin not requiring a synthetic binding agent. The sheet is believed to be bound together by reformed disulfide linkages and hydrogen bonds. A preferred use of the sheet is as a wound healing dressing. Another preferred use is as a tissue engineering cell scaffold for implant applications. The sheet can be formed from a combination of soluble and insoluble protein fractions derived from hair, including alpha and beta keratin fractions. Keratin can be obtained from a number of sources, including human or animal hair and finger or toe nails, with one source being hair of the patient or a donor.

The sheet can be formed by providing an insoluble chemically modified keratin fraction suspended in water and lowering the pH until the keratin protein is partially swelled. Partially swelled is defined as the protein molecule swelling such that the resulting suspension of keratin particles behaves like a colloidal suspension. In one method, concentrated sulfuric acid is added until a pH of less than 1 is reached. Applicants believe the low pH disrupts the hydrogen bonds which have been rendering the keratin fraction insoluble, thereby allowing the protein to partially swell. The partially swelled keratin is then made basic with ammonium hydroxide. This treatment exchanges the non-volatile acid with a volatile base, which is removed upon drying. Alternatively, a volatile acid, such as formic acid, may be employed, eliminating the requirement for further treatment with a volatile base. The resulting slurry can then be cast onto a flat surface or mold of appropriate geometry and surface finish and air dried to produce a cross-linked keratin sheet. Applicants believe the cross-links result from the thiol groups re-forming disulfide linkages and from the amine, and carboxylic acid groups forming hydrogen bonds.

The resulting sheet is thus formed of pure keratin. Keratin has been shown to be biocompatible, non-immunogenic, not to inhibit activated T-cells and therefore not interfere with the normal cell mediated immune response, and to be mitogenic for keratinocytes, fibroblasts, and human microvascular endothelial cells. Keratin has also been shown to promote epithelialization in wound healing studies on rats and humans.

Another embodiment of the invention includes partially oxidizing the keratin disulfide linkages to form hydrophilic groups. One such method includes treating the keratin with peractic acid to form sulfonic acid groups from a substantial portion, but not all of, the disulfide bonds. Most of the sulfonic acid groups remain in the final product as hydrophilic groups, binding water and hydrating the keratin material. A later reduction step cleaves many of the remaining disulfide bonds to form cysteine residues. The partially oxidized and reduced keratin can then be in put in solution, concentrated, and cast onto a flat surface to oxidize and re-form disulfide cross-links. In one method, oxygen in air acts as the oxidizing agent, with the keratin being air dried to form a film on the flat surface. The moist keratin sheet, consisting primarily of keratin derived from beta keratin, has the consistency of moist, thick paper. The sheet dries to a brittle material, which can be rehydrated to a supple, skin-like material. The rehydrated sheet has the look and feel of skin while retaining moisture within the sheet and within the wound. The sheet can be used as a wound-healing dressing or as a cell-growth scaffold. The sheet can be cut and shaped as needed before being applied to the wound. The keratin sheets provide a non-antigenic wound dressing that maintains wound moisture for migrating epithelial cells and provides a scaffold for cell growth for tissue engineered implants. Other applications for this keratin sheet include use as diffusion membranes and as an encapsulant for cells.

The present invention includes methods for forming keratin based thin films, open cell foams, and bulk materials. The thin films are suitable for use as wound dressings, tissue-engineering scaffolds, diffusion membranes, coatings for implantable devices, and cell encapsulants. In one method, cut, washed, rinsed, and dried vertebrate hair is provided. The hair is reduced with a reducing agent, such that some of the disulfide linkages are broken, and a more soluble keratin fraction and a less soluble keratin fraction formed. The more soluble keratin fraction is separated, collected, and deposited onto a surface, thereby forming a layer of the more soluble keratin fraction. The keratin layer is exposed to an oxidizing agent, such as air, oxygen, or $H_2O_2$, and preferably dried. The free thiol groups are oxidized by the oxidizing agent, the resulting keratin film being strengthened by the newly formed disulfide bonds. A higher degree of crosslinking, and therefore strength, can be obtained by the addition of crosslinking agents such as glutaraldehyde.

In one method according to the present invention, a keratin solution is provided, the keratin being dissolved in a first solvent such aqueous thioglycolate. The keratin has free thiol groups, produced by methods such as reduction with ammonium thioglycolate. A second solvent such as hexane or Freon is provided, the second solvent preferably being substantially immiscible in the first solvent and the keratin preferably being substantially insoluble in the second solvent. An emulsion of the second solvent in the keratin solution can be formed using a homogenizer. The emulsion is freeze dried, preferably by freezing the emulsion and removing the first and second solvents under vacuum, creating a porous keratin material. The porous keratin material can be warmed to room temperature in the presence of an oxidizing agent, promoting the formation of disulfide crosslinks between the keratin. In one method, the oxidizing agent is an oxygen containing gas such as air. In another method, hydrogen peroxide is mixed with the keratin solution prior to homogenizing. Applicants believe the resulting material is an open cell scaffold having substantially spherical voids corresponding to the second solvent in the emulsion and a cross-linked keratin structure corresponding to the keratin solution in the emulsion.

In another method according to the present invention, a keratin solution is provided, the keratin being dissolved in a solvent such aqueous thioglycolate. The keratin has free thiol groups, produced by methods such as reduction with ammonium thioglycolate. The keratin can be atomized and sprayed onto a very cold surface, sufficiently cold to freeze the keratin solution. In one method, the surface is the surface of a mold. More keratin solution can be atomized and sprayed over the already frozen keratin, thereby building up a thicker open cell layer of frozen keratin. The frozen keratin can be freeze dried by removing at least a substantial portion of the solvent, and preferably all of the solvent, under low pressure at low temperature. The keratin material can be warmed to room temperature in the presence of an oxidizing agent, promoting the formation of disulfide cross-links within the keratin solids formed and between the keratin solids formed. In one method, the oxidizing agent includes gaseous oxygen. In another method, the oxidizing agent includes hydrogen peroxide added to the keratin solution. Applicants believe the resulting structure is an open cell scaffold having substantially spherical keratin structures corresponding to the atomized keratin and having voids therebetween. Applicants believe the substantially spherical keratin structures have disulfide cross-links formed within, and the structures have disulfide cross-links between structures where touching each other.

In one method, according to the invention, hair is cut, washed, dried, and suspended in ammonium hydroxide containing ammonium thioglycolate. The suspension is under a nitrogen atmosphere. The basic ammonium thioglycolate solution serves to solubilize the keratin and reduce the disulfide cross-links. Cysteine thiol groups and cysteine thioglycolate groups are formed from the broken disulfide bonds. The nitrogen atmosphere serves to prevent oxidation and reformation of disulfide bonds. Heating is preferably followed by comminuting the hair particles with a tissue homogenizer followed by further heating under a nitrogen atmosphere. A fine keratin suspension results.

The fine keratin suspension is centrifuged, and the supernatant containing a more soluble keratin fraction is collected and precipitated out with acid. The precipitate is resuspended in ammonium hydroxide. The keratin solution is then cast as a thin film on a surface and allowed to air dry. The air serves to remove water, concentrate the keratin, and oxidize the cysteine thiol groups, forming disulfide bridges and strengthening the film. Further crosslinking can be achieved using chemical means such as glutaraldehyde. The resulting film is tough and insoluble.

In one method, cut, washed, rinsed, and dried vertebrate hair is provided. The hair is reduced with a reducing agent, such that some of the disulfide linkages are broken, and a more soluble keratin fraction and a less soluble keratin fraction formed. The more soluble keratin fraction is separated, collected, and concentrated, and the more soluble keratin fraction is deposited into a mold. The concentrated keratin solution in the mold is exposed to an oxidizing or crosslinking agent and preferably dried. The free thiol groups are oxidized by the oxidizing agent or crosslinked by the crosslinking agent, and the keratin strengthened by newly formed disulfide bonds. In another method, the concentrated keratin solution is either atomized into a cold mold or mixed with a polar solvent, emulsified, and freeze-dried to form an open-cell material. The keratin solution is exposed to an oxidizing or crosslinking agent, which crosslinks and strengthens the material. A porous keratin material remains.

In another method according to the present invention, the more soluble keratin solution is further concentrated, for example, by air drying or heating under sub-ambient pressure. The concentrated solution is poured into a mold and allowed to air dry. The air serves to remove water, concentrate the keratin, and oxidize the cysteine-thiol groups, forming disulfide bridges and strengthening the keratin material. The resulting bulk keratin material is tough and insoluble. In another method, a liquid oxidizing agent such as hydrogen peroxide is used. In yet another method, a crosslinking agent such as glutaraldehyde is used.

DETAILED DESCRIPTION OF THE PREFERRED EMBODIMENTS

Keratin Preprocessing

In one method according to the present invention, hair is provided, preferably washed and unbleached. The hair can be harvested from a human or animal source. The patient or a human donor is a preferred source of hair for some medical applications, as hair from these sources is most likely to result in a non-antigenic product, although animal hair may be acceptable for certain individuals that do not have animal product allergy problems. In one method, the hair is washed with Versa-Clean™ (Fisher Scientific, Pittsburgh, Pa.), rinsed with deionized water, and allowed to air dry.

Partial Oxidation of Keratin

The hair can be oxidized in peracetic acid or another suitable reagent such as $H_2O_2$. A preferable treatment utilizes from 1% to 32% peracetic acid, at a temperature between about 0° C. and 100° C. for between 0.5 and 24 hours. One method treats 30 grams of hair with 500 mL of 32% peracetic acid at 4° C. for 24 hours. This treatment with peracetic acid partially oxidizes the naturally occurring disulfide linkages to produce a protein with cysteic acid ($—CH_2SO_3H$) residues and remaining disulfide linkages. The hair is recovered, preferably by filtration through a coarse fritted glass filter, and rinsed numerous times with deionized water until the rinse solution has a pH of 6.0 or higher. The hair can then be dried in a vacuum oven at between 20° C. and 50° C. for between 0.5 and 5 days. One method dries the hair in a vacuum oven at 40° C. for several days. The dried hair can then be pulverized and ground into a fine powder. One method of grinding the hair uses a ceramic mortar and pestle.

Reduction of Partially Oxidized Keratin

The keratin powder can be suspended in ammonium thioglycolate. In one method, pulverized keratin powder, derived from hair as described above, is suspended in about 3N ammonium hydroxide containing ammonium thioglycolate. About 6 grams of keratin powder can be added per 75 mL of ammonium hydroxide. The strength of ammonium hydroxide is preferably about 3N, and the preferred concentration of ammonium thioglycolate is about 11 mL (as thioglycolic acid) per 75 mL of ammonium hydroxide. The suspension can then be heated for a time sufficient to solubilize the soluble fraction of the hair. The suspension, in one method, is heated between 50° C. and 90° C. for between 1 and 24 hours, followed by cooling. According to another method, the suspension is heated to about 60° C. for about 4 hours and cooled to room temperature. This treatment cleaves the remaining disulfide linkages to produce cysteine residues in the protein structure. At this point, the keratin protein contains both cysteic acid residues and cysteine residues. The ratio of cysteic acid residues and cysteine residues can be controlled by varying the time, temperature, and concentration of oxidant in the peracetic acid treatment step previously described. The presence of sulfonic acid residues imparts a hydrophilic property to the hair, as well as the final sheet product.

Separation of Partially Oxidized. Reduced Keratin

After the oxidation/reduction treatment described above, a resistant keratin fraction remains, consisting primarily of beta keratin. This keratin fraction is preferably at least 80% beta keratin, most preferably greater than about 90% beta keratin. This fraction is insoluble in the suspension and is removed in one method by centrifugation at about 10,000 g for about 10 minutes. A thick, jelly-like supernatant remains and is discarded or, more preferably, kept for another use. The remaining insoluble fraction is composed mostly of the original cuticle (outer layer of hair shaft) and is composed primarily of beta keratin.

Acidification of Partially Oxidized, Reduced Keratin

The insoluble material is transferred to another container and acidified to a low pH. The pH is preferably less than about 3 and most preferably less than about 1. In one method the pH is less than about 1 and the acid used can be either concentrated sulfuric acid or formic acid. This treatment disrupts hydrogen bonding of the cuticle structure of the hair shaft. The low pH disrupts the hydrogen bonds responsible for tightly binding the keratin protein, resulting in its resistance to chemical modification. Applicants believe the acid at least partially unfolds or swells the protein, enhancing the solubility. The slurry preferably has a concentration in the range of 0.001 grams/mL to 0.6 grams/mL. The slurry most preferably has a concentration in the range of 0.2 grams/mL to 0.3 grams/mL.

Neutralization, Concentration and Oxidation of Partially Oxidized, Reduced Keratin The unfolded or swelled keratin slurry can then be made slightly basic with ammonium hydroxide, preferably about 6N strength. The slurry can then be cast onto a flat surface and air dried to produce the cross-linked sheet. A preferred relative humidity range for drying is between 0% and 90%. The relative humidity is most preferably between about 40% and 60% relative humidity. The partially unfolded, swelled, and partially solubilized keratin refolds upon addition of the base during drying, causing hydrogen bonding of the keratin. The free thiol groups form disulfide linkages.

The insoluble keratin fraction from hair is thus treated so as to have both sulfonic acid groups and thiol groups, and is separated from the soluble fraction. The insoluble fraction is treated with acid to partially unfold, swell, and solubilize the keratin, followed by treatment with base and casting onto a flat surface to refold the protein and form some disulfide bonds.

In an alternate method, in the acidification step, the keratin is suspended in a volatile acid, such as formic acid, having sufficiently low pH to partially unfold or swell the keratin protein. In this method, the treatment with volatile base can be dispensed with. The acidification step can be immediately followed by forming the keratin slurry into a sheet.

The resulting sheet may be cleansed of soluble reagents by repeated treatment with hot (boiling), deionized water, yielding a cross-linked, pure keratin sheet. The moist keratin sheet, formed of keratin derived primarily from beta keratin, has the consistency of moist paper. The sheet produced will dry to a brittle material which can be rehydrated to a supple skin-like material, suitable for use as a sheet wound dressing. The sheet retains water and the rehydrated sheet has the look and feel of skin. In a preferred method of use, the sheet is hydrated sufficiently to allow the sheet to be draped over a wound.

Keratin Slurry Including Partially Oxidized Alpha and Beta Keratin Fractions

In an alternate embodiment of the present invention, the keratin centrifugation step used to separate the soluble and insoluble partially oxidized keratin fractions is omitted and both fractions are used in further processing. In one embodiment, both fractions are further processed together with acid as described above. In this method, both soluble and insoluble fractions are transferred to another container and acidified to a low pH. The unfolded or swelled keratin slurry can then be made slightly basic with ammonium hydroxide, preferably about 6N strength. The slurry can then be cast onto a flat surface and air dried to produce a cross-linked sheet. As an alternate method, in the acidification step, the keratin is suspended in a volatile acid, such as formic acid, as described previously. In this method, the treatment with volatile base can be dispensed with. In one method, the thick slurry having both keratin fractions can be cast into a thin film as previously discussed. The resulting product has a somewhat smoother texture than a pure beta keratin derived product. In another method, the thick slurry can be further concentrated and used to form a bulk keratin product as discussed below.

Use of Partially Oxidized Alpha Keratin Fraction

In one embodiment, the keratin in the keratin solution is at least 90% keratin derived from alpha keratin. The resulting keratin solution containing partially oxidized keratin derived primarily from alpha keratin can be utilized as described above, in the formation of films and sheets. The alpha keratin found in hair is primarily crystalline prior to processing, but is primarily amorphous after processing and cross-linking. Thus the terms "alpha" and "beta" refer to the keratin protein structures at the source, not necessarily the keratin protein structures after processing and cross-linking. The alpha keratin is derived primarily from hair cortex keratin while the beta keratin is derived primarily from hair cuticle keratin. A preferred method utilizes hair cortex keratin.

In another embodiment, the soluble keratin fraction is used to form a sheet or film. After centrifugation such as described above, the insoluble fraction can be set aside for other use. A thick, jelly-like supernatant remains, which includes a soluble, partially oxidized keratin fraction derived primarily from alpha keratin. The keratin fraction is termed "soluble" as it is soluble in a basic, aqueous solution. In a preferred method, "soluble" keratin refers to a keratin fraction soluble at a pH of 10 or greater, but which may be soluble at lower, basic pH. In a preferred method, "insoluble" keratin refers to keratin insoluble at a pH of 10. The supernatant is collected. The supernatant can be treated with concentrated HCl until a gummy precipitate is produced. The precipitate can be collected, washed with deionized water, and dissolved in 15 mL of 3N ammonium hydroxide, forming a keratin solution.

Keratin Sheet Applications

Applicants believe the keratin product made according to this method is suitable for use as a cell-growth scaffold that is mitogenic and as a nutrient support for cell growth. Applicants also believe the cross-linked keratin sheet can be used as a scaffold material for a variety of cells, including skin component cells (keratinocytes, fibroblasts, endothelial cells), osteoblasts, chondrocytes, and hepatocytes. In particular, applicants have shown that skin component cells will grow and proliferate favorably on the keratin sheet. Applicants further believe the keratin sheet can be used as a diffusion membrane and to encapsulate cells for various applications.

Anti-bacterial additives, ointments, and biologicals such as growth factors or collagen can be added to the keratin sheet. Bactericidal ointment or a suspension of antibiotics or biologicals can be impregnated into the sheet dressing by passing a blade having the additive at its front over the sheet, thereby evenly distributing the additive over the sheet. Alternatively, the sheet material can be soaked in a solution containing the desired additive and the additive allowed to precipitate onto the surface of the sheet. The solvent can then be flashed off, leaving the sheet material impregnated and coated with the desired additive.

Keratin Reduction without Previous Partial Oxidation Step

Clean, keratin-containing hair prepared as previously described can be suspended in a reducing agent. A preferred reducing agent is ammonium thioglycolate. Other reducing agents believed suitable for use in the present invention include mercaptoethanol, dithiothreitol, thioglycerol, thiolactic acid, glutathione, cysteine, and sodium sulfide. In one method, the washed and cut hair, as described above, is suspended in about 3N ammonium hydroxide containing ammonium thioglycolate. The ammonium hydroxide is believed to deprotonate the carboxylic acids and the cysteine thiol groups, forming a polyanionic polymer having increased solubility in water. The ammonium hydroxide is believed to partially swell the keratin protein, exposing additional disulfide linkages to reaction with thioglycolic acid. About 6 grams of hair can be added per 75 mL of ammonium hydroxide. The strength of ammonium hydroxide is preferably about 3N and the preferred concentration of ammonium thioglycolate is about 11 mL (as thioglycolic acid) per 75 mL of ammonium hydroxide. The suspension can then be heated for a time sufficient to solubilize the soluble fraction of the hair. The suspension in one method is heated between 50° C. and 90° C. for between 1 and 24 hours, followed by cooling. In a preferred method, the suspension is heated to about 60° C. for about 2 hours under a nitrogen atmosphere and homogenized with a tissue homogenizer, as will be described in detail in the next section, for about 30 minutes until a fine dispersion is produced.

Homogenizing/Comminuting of Reduced Keratin

Homogenizing, as the term is used herein, refers to the hair particles being comminuted, that is, broken down into smaller particles using a rotor/stator combination homogenizer blade. The reduced hair was homogenized in situ in the ammonium thioglycolate solution using procedures described in U.S. Pat. No. 5,358,935 (without using liquid $N_2$) incorporated by reference above. Hair is protected by a tough outer keratin layer resistant to chemical treatment. The outer layer is formed of primarily beta keratin material. The homogenizing separates the outer, protective cuticle material from the inner, cortex material and comminutes the hair to make small keratin particles. The cortex contains keratins moderately soluble in water, but keratins not normally exposed to water, lying within the protective cuticle. The cortex contains primarily alpha keratin. The homogenization also exposes disulfide bonds to reactants such as thioglycolate. The dispersion in one method is further heated an additional two hours at 60° C. under a nitrogen atmosphere before being cooled to room temperature. The continued heating step provides time for the ammonium thioglycolate to break and reduce the newly exposed cysteine disulfide linkages. A thick slurry is the expected result in a preferred method. The heating speeds up the reduction of disulfide bonds. The nitrogen atmosphere prevents the oxidation of thiol groups by atmospheric oxygen. Applicants believe this treatment cleaves disulfide linkages to produce cysteine and cysteinethioglycolate disulfide residues in the protein structure.

Separation

After the treatment described above, a keratin fraction resistant to the treatment remains, consisting primarily of beta keratin. This fraction is insoluble in the suspension and is removed in one method by centrifugation at about 10,000 g for about 10 minutes. The insoluble fraction can be set aside for other use. A supernatant remains, which includes a soluble keratin fraction derived primarily from alpha keratin. The keratin fraction is termed "soluble" as it is soluble in a basic, aqueous solution. In a preferred method, "soluble" keratin refers to a keratin fraction soluble at a pH of 10 or greater, but which may be soluble at lower, basic pH. In a preferred method, "insoluble" keratin refers to keratin insoluble at a pH less than 10. The supernatant is collected. The supernatant can be treated with concentrated HCl until a gummy precipitate is produced. The precipitate can be collected, washed with deionized water, and dissolved in 15 mL of 3N ammonium hydroxide, forming a keratin solution.

In one embodiment, the keratin in the keratin solution is at least 90% keratin derived from alpha keratin. The alpha keratin found in hair is primarily crystalline prior to processing but is primarily amorphous after processing and cross-linking. Thus the terms "alpha" and "beta" refer to the keratin protein structures at the source, not necessarily the keratin protein structures after processing and cross-linking. The alpha keratin is derived primarily from hair cortex keratin while the beta keratin is derived primarily from hair cuticle keratin. Hair cuticle keratin typically includes substantial color from the original hair. Hair cortex keratin does not include the original hair color. A preferred method utilizes hair cortex keratin.

Film and Sheet Formation

The solution can be cast into a thin film and allowed to air dry into a cross-linked film derived primarily from alpha keratin. The keratin re-forms disulfide bonds, giving the film added strength. Weaker bonds, such as hydrogen bonds, also impart strength to the keratin-based film as the solution becomes more concentrated, bringing the keratin proteins in closer proximity to one another. In one method, the solution is poured onto a flat surface, for example a glass surface. In another method, the solution is poured onto a rotating drum or moving belt. Pouring the solution onto a flat surface produces a thin, flat geometry resembling that of the final film. Forming the flat surface also creates a high surface to volume ratio, allowing air to penetrate into the solution a substantial fraction of the total depth and volume.

Concentration and Oxidation

Air drying performs several functions. First, the air removes water, thereby concentrating the keratin solution. The more concentrated solution increases the rate of formation and number of re-formed disulfide bonds. The disulfide bonds formed or reformed are not necessarily between the same cysteine groups in the initial protein. Second, the air contains oxygen, which oxidizes the free thiol groups in the protein, forming disulfide bonds. Other oxidizing gases can be used in place of air, for example oxygen. Oxidizing liquids such as hydrogen peroxide are also suitable for oxidizing the free thiol groups. Third, the air allows the ammonium hydroxide to evaporate. The resulting lowered pH also helps reform the disulfide bonds. Fourth, the air allows some excess thioglycolate to escape. When the film formation is carried out in the presence of nitrogen rather than air, applicants believe the film formed has far fewer disulfide bonds, but that the film is bound with hydrogen bonds, resulting in a film that is softer than the film formed in the presence of oxygen. The resulting residual thiol activity would provide sites for the incorporation of desirable thiol-containing biological factors.

The concentration and oxidation causes the formation of a tough, insoluble material. Excess thioglycolate, and the disulfide of thioglycolic acid, may remain in the film and can be removed through extraction in boiling water. In one method of cleaning, the film is immersed in boiling water for about 1.5 hours, changing the water every 15 minutes. This cleaning is believed to remove mostly excess, unreacted thioglycolate as opposed to thioglycolate bound to the protein backbone.

Slow evaporation can also be used to remove ammonium hydroxide from the material, thereby lowering the pH and promoting cross-link formation. Reducing pH in itself causes increased cross-linking and precipitation of protein. An additional crosslinking agent such as glutaraldehyde can be used to form cross-inks other than disulfide crosslinks. The use of glutaraldehyde allows cross-linking without requiring the same degree of concentration or water removal as required for cross-linking relying primarily on disulfide bond formation and could also increase the final degree of crosslinking over the oxidation crosslinking procedure.

Another method for forming the disulfide cross-links includes the steps of removing the water and ammonium hydroxide under vacuum. In one method, the soluble keratin fraction in solution is placed into a chamber and a vacuum pulled on the chamber, removing much of the water from the material. The water is volatilized at a low temperature, leaving behind a cross-linked keratin material.

Uses

Applicants believe the resulting material can be formed into a thin film, wound dressing, or tissue-engineering scaffold. Another use is as a diffusion membrane, for example, for drug delivery. Yet another use is for coating implantable devices, such as stents and maxillofacial implants, with the non-antigenic cross-linked keratin film material. The parts to be coated can be dipped in the keratinous solution, followed by air drying or other method to promote cross-linking. This gives strong adherence to the implant since cross-linking occurs on the actual implant shape as a thin film. Yet another use is as an encapsulant to encapsulate cells. Individual cells can be encapsulated, allowing, for example, the film to act as a nutrient supply, a mitogen, or a diffusion membrane.

Further Concentration

In another method embodying the present invention, the resulting keratin suspension is further concentrated. The resulting solution is preferably concentrated to a concentration of between about 0.1 and 0.5 grams per mL, more preferably between about 0.3 and 0.4 grams per mL, and most preferably about 0.35 grams per mL. The concentrated keratin solution can be used to create a porous, open cell keratin scaffold, discussed in detail below, in the open cell section.

Keratin Slurry Including Alpha and Beta Keratin Fractions

In an alternate embodiment of the present invention, the keratin centrifugation step used to separate the soluble and insoluble keratin fractions is omitted, and both fractions are used in further processing. In one method, the thick slurry having both keratin fractions can be cast into a thin film as previously discussed. The resulting product has a somewhat rougher texture than the pure alpha keratin derived product. In another method, the thick slurry can be further concentrated and used to form a bulk keratin product as previously discussed.

Keratin Slurry Including Alpha and Beta Keratin Fractions with Further Acid Treatment In another embodiment of the present invention, the keratin centrifugation step used to separate the soluble and insoluble keratin fractions is omitted, and both fractions are further processed with acid. In this method, both soluble and insoluble fractions are transferred to another container and acidified to a low pH. The pH is preferably less than about 3 and most preferably less than about 1. In one method, the pH is less than about 1, and the acid used can be hydrochloric, concentrated sulfuric, or formic acid. Applicants believe the acid at least partially swells the protein, enhancing the solubility of the insoluble fraction. The slurry preferably has a concentration in the range of 0.001 grams/mL to 0.6 grams/mL. The slurry most preferably has a concentration in the range of 0.2 grams/mL to 0.3 grams/mL.

The unfolded or swelled keratin slurry can then be made slightly basic with ammonium hydroxide, preferably about 6N strength. The slurry can then be cast onto a flat surface and air dried to produce the cross-inked sheet. A preferred relative humidity range for drying is between 0% and 90%. The relative humidity is most preferably between about 40% and 60% relative humidity. The partially unfolded or swelled, partially solubilized keratin refolds upon addition of the base during drying, causing hydrogen bonding of the keratin. The free thiol groups form disulfide linkages. In an alternate method, glutaraldehyde can be added to the partially solublized keratin to provide an increased degree of crosslinking. As an alternate method, in the acidification step, the keratin is suspended in a volatile acid, such as hydrochloric or formic acid, having sufficiently low pH to partially swell the keratin protein. In this method, the treatment with volatile base can be dispensed with. The acidification step can be immediately followed by forming the keratin slurry into a sheet. The keratin slurry can also be further concentrated for production of bulk keratin.

Keratin Slurry Including Primarily Beta Keratin with Further Acid Treatment

In another embodiment of the present invention, the keratin centrifugation step used to separate the soluble and insoluble keratin fractions is performed and the beta fraction is further processed with acid. In this method, the insoluble fraction is transferred to another container and acidified to a low pH. The pH is preferably less than about 3 and most preferably less than about 1. In one method, the pH is less than about 1 and the acid used can be hydrochloric, concentrated sulfuric, or formic acid. Applicants believe the acid at least partially swells the protein, enhancing the solubility of the insoluble fraction. The slurry preferably has a concentration in the range of 0.001 grams/mL to 0.6 grams/mL. The slurry most preferably has a concentration in the range of 0.2 grams/mL to 0.3 grams/mL.

The keratin slurry can then be made slightly basic with ammonium hydroxide, preferably about 6N strength. The slurry can then be cast onto a flat surface and air dried to produce the cross-linked sheet. A preferred relative humidity range for drying is between 0% and 90%. The relative humidity is most preferably between about 40% and 60% relative humidity. The partially unfolded, swelled, partially solubilized keratin refolds upon addition of the base during drying, causing hydrogen bonding of the keratin. The free thiol groups form disulfide linkages. In an alternate embodiment, glutaraldehyde can be added to the partially solublized keratin to provide an increased degree of crosslinking. As an alternate method, in the acidification step, the keratin is suspended in a volatile acid, such as formic acid, having sufficiently low pH to partially swell the keratin protein. In this method, the treatment with volatile base can be dispensed with. The acidification step can be immediately followed by forming the keratin slurry into a sheet. The keratin slurry can also be further concentrated for production of bulk keratin.

Keratin Open Cell and Bulk Materials

The present invention also includes methods for forming keratin bulk materials and porous open cell materials. The bulk material is suitable for use as a cross-linked implantable device, which can be used for maxillofacial restoration, for example, for soft and hard tissue replacement. The bulk material can also be used for orthopedic applications such as bone filler and cartilage regeneration. A tubular form of the implanted material can also be used for neurological applications such as nerve regeneration guides. The porous keratin material can be used as a tissue-engineering scaffold.

The invention includes processes for forming solid and porous bulk keratin materials. A keratinous material, such as human hair, is provided. The hair is suspended in liquid and reduced with a reducing agent, breaking the disulfide bonds. A keratinous slurry is the preferred result. The slurry, which can be further processed and purified, is preferably further concentrated and deposited into a mold to form a solid part in the shape of the mold. Alternatively, the slurry can be used to process open cell, foam materials using a variety of methods described in the literature. One technique uses a spray of the atomized keratin solution on the surface of a cooled mold, thereby building up a foam structure as described by Lo et al. for PLLA foam fabrication (H. Lo, S. Kadiyala, S. E. Guggino, and K. W. Leong, "Poly (L-lactic acid) foams with cell seeding and controlled-release capacity," J. Biomed. Mater. Res., Vol. 30, pp. 475–484, 1996). A second technique, also developed for PLA/PGA polymers, uses freeze drying emulsions of polymer solutions to process open cell polymer structures (K. E. Healy, K. Whang, and C. H. Thomas, "Method of fabricating emulsion freeze-dried scaffold bodies and resulting products," U.S. Pat. No. 5,723,508, issued Mar. 3, 1998). A similar process can be modified using the appropriate solvents and conditions to make an open cell keratin scaffold. For example, the keratin is dissolved in a volatile non-polar solvent and mixed with a volatile polar solvent in which the keratin is insoluble. These two solvents are immiscible. An emulsion is generated using ultrasound or a homogenizer, frozen, and freeze-dried to remove the solvents. An oxidizing agent, such as air or a peroxide or a crosslinking agent such as glutaraldehyde, can be supplied to the keratin material in the emulsion stage. The keratin concentration and oxidizing agent act to promote keratin cross-linking. The resulting keratin cross-linked product is hard and porous, with a microstructure dependent on the exact method used.

Numerous characteristics and advantages of the invention covered by this document have been set forth in the foregoing description. It will be understood, however, that this disclosure is, in many respects, only illustrative. Changes may be made in details, particularly in matters of shape, size, choice of reagents, and ordering of steps without exceeding the scope of the invention. The invention's scope is, of course, defined in the language in which the appended claims are expressed.

Experimental Results, Partially Oxidized Keratin Product

In a first experiment, a sheet wound dressing not requiring a binder was prepared from keratin derived from human hair. Human hair was obtained from males aged 10 to 30 years, washed with Versa-Clean™ (Fisher Scientific, Pittsburgh, Pa.), rinsed with deionized water and allowed to air dry. This hair was subsequently chopped into approximately 0.25-inch to 2-inch lengths using shears. Thirty grams of this hair was treated with 500 mL of 32% peracetic acid (Aldrich Chemical, Milwaukee, Wis.) at 4° C. for 24 hours. This treatment partially oxidized the disulfide linkages. The hair was recovered by filtration through a coarse fritted glass filter and rinsed numerous times with deionized water until the rinse solution was pH 6.0 or higher. The hair was dried under ACLU at 40° C. for several days until completely dry and ground to a fine powder with a ceramic mortar and pestle. The resulting material, 19 grams, was further modified to produce a flexible, hydratable sheet composed primarily of beta keratin.

Six grams of the pulverized, oxidized hair was suspended in 75 mL of 3N ammonium hydroxide containing 11 mL of ammonium thioglycolate (as thioglycolic acid). The suspension was heated to 60° C. for 4 hours and then cooled to room temperature. This treatment cleaved the remaining disulfide linkages to produce cysteine residues in the protein structure. An insoluble fraction remained, which was resistant to solubilization by the ammonium hydroxide and ammonium thioglycolate. The insoluble fraction, comprised mostly of beta keratin, was isolated by centrifugation at 10,000 g for 10 minutes. A thick, jelly-like supernatant was removed from the centrifuged material and set aside.

The remaining insoluble fraction is composed mostly of the original cuticle (outer layer of hair shaft) and is composed primarily of beta keratin. The insoluble material was transferred to a flask and acidified to a pH of between 0 and about 1 with concentrated sulfuric acid. The partially unfolded keratin was made slightly basic with 6N ammonium hydroxide. The slurry was then cast onto a flat surface and air dried to produce a crosslinked sheet. The resulting sheet was purified by immersion in boiling water, which removed soluble reagents.

The use of keratin-containing materials in promoting wound healing was demonstrated in several experiments. In a first experiment, processed human hair was incubated with cell culture media. The media/hair mixture was passed through a micro filter. Cell lines relevant to wound healing, including human microvascular endothelial cells, keratinocytes, and fibroblasts, were placed in cultures using this media extract. Significant proliferation of these wound healing cells was measured. Keratinocytes proliferated profusely, fibroblasts proliferated modestly, and endothelial cells proliferated profusely.

The mitogenic activity observed in fibroblast, keratinocyte, and endothelial cell cultures is additional evidence that the keratinous protein material is not only biocompatible, but also mitogenic with these cell lines. Additional biocompatibility was observed when keratin microfibrils were observed microscopically to be in direct contact with cells in the cell cultures. Specifically, keratinocytes and fibroblasts were observed to adhere to and congregate around microfibrils, indicating that desirous cell activity can be sustained on this naturally derived biopolymer matrix.

In a second experiment, processed human hair powder was incubated with cell culture media. The media/keratin mixture was passed through a micro filter. This media extract was used in proliferation studies with lymphocytes. The lymphocyte cell line did not proliferate, indicating the material to be non-immunogenic.

In a third experiment, processed human hair powder was incubated with cell culture media. The media/hair mixture was then passed through a micro filter. This media extract was used in proliferation studies with activated T-lymphocytes. The T-lymphocytes proliferated normally, indicating no inhibition of the normal cell mediated immune response by the keratin. This demonstrated no inhibition of this very important function of immune cells.

In a fourth experiment, twenty-eight hairless rats were wounded on either side of the dorsal midline with a dermatome, creating a partial thickness wound 0.12 inches in depth, and 2.0×4.0 cm in surface area. Half the wounds were treated with keratin powder, half were not, and both halves were covered with polyurethane dressing. The wounds were observed for healing and biopsied at days 0, 2, 4 and 6 for histochemical analysis. Planimetry studies showed 97% epithelialization of the keratin-treated wounds and 78% epithelialization of the non-treated wounds at day 4. Histological analysis by H & E stain revealed total epithelialization microscopically of the keratin-treated wounds at day 2 and only partial epithelialization of the non-treated wounds at day 2. Histological analyses at days 4 and 6 also revealed an acceleration of the epithelialization maturation process in the keratin-treated wounds.

Human clinical studies are currently being performed on donor sites for skin grafts. One half of the donor wound site is treated with sterilized keratin powder and the opposite half treated in a standard fashion, with Adaptic™ non-adhering dressing from Johnson & Johnson. Preliminary results show the keratin-treated halves epithelialize sooner and mature more rapidly. This was confirmed through both clinical observations and histological results of four-millimeter punch biopsies. Subjectively, patients also have much less pain in the keratin-treated wounds.

Experimental Results, Keratin Product Without Partial Oxidation

In a fifth experiment, human hair was obtained from males aged 10 to 30 years, washed with Versa-Clean™ (Fischer Scientific, Pittsburgh, Pa.), rinsed with deionized water and allowed to air dry. This hair was subsequently chopped into approximately 0.25" to 2" lengths using shears. Six grams of hair was suspended in 75 mL of 3N ammonium hydroxide containing 11 mL of ammonium thioglycolate. This treatment cleaved the disulfide cystine linkages to produce cysteine residues in the protein structure. The suspension was heated to 60° C. for 2 hours under a nitrogen atmosphere and then homogenized with a tissue homogenizer for 30 minutes until a fine dispersion was produced. The dispersion was heated an additional 2 hours at 60° C. under a nitrogen atmosphere and then cooled to room temperature. The thick slurry was transferred to a tube and centrifuged at 5000 G for 10 minutes. The supernatant was treated with concentrated hydrochloric acid until a gummy precipitate was produced. The precipitate was collected, washed with deionized water and then dissolved in 15 mL of 3N ammonium hydroxide.

This solution was then cast into a thin film and allowed to air dry. The solution was also further concentrated through evaporation, and cast into a solid block of material. The removal of the volatile base and water from the solution and the action of the air upon the free thiol fraction of the soluble polypeptide caused the material to crosslink into an insoluble, tough material. The material was then purified and freed of any remaining thioglycolic acid by extraction in boiling water for 1.5 hours.

In a sixth experiment, human hair was chemically treated as previously described. This produced a keratin solution that was then cast into a sheet and oxidatively cross-linked to produce a non-soluble sheet of keratin. The sheet was purified by extraction with boiling water for 1.5 hours, changing the water every 15 minutes. Segments of the sheeting were then incubated with keratinocytes, fibroblasts, and human microvascular endothelial cells. These cells were shown to grow and proliferate favorably on the keratin sheet. This indicates that skin component cells proliferate favorably in the presence of keratin sheeting produced by the above-described method.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method for making a porous, cross-linked keratin material comprising the steps of:

providing a keratin solution including keratin in solution in a first solvent, said keratin having free thiol groups;

providing a second solvent, said second solvent being substantially immiscible in said first solvent, wherein said keratin is substantially insoluble in said second solvent;

providing an oxidizing agent;

emulsifying said keratin solution and said second solvent together;

freezing said emulsion;

removing a substantial portion of said first and second solvents under vacuum and low temperature, such that a porous keratin material is created; and warming said porous keratin material in the presence of said oxidizing agent, such that said porous keratin free thiol groups are oxidized to form disulfide cross-links and cross-link said porous keratin material.

2. A method as recited in claim 1, wherein said emulsion includes said second solvent emulsified in said keratin solution and said oxidizing agent includes gaseous oxygen.

3. A method as recited in claim 1, wherein said emulsion includes said second solvent emulsified in said keratin solution and said oxidizing agent is provided in said keratin solution.

4. A method as recited in claim 3, wherein said oxidizing agent includes hydrogen peroxide.

5. A porous, cross-linked keratin material created by the process comprising the steps of:

providing a keratin solution including keratin in solution in a first solvent, said keratin having free thiol groups;

providing a second solvent, said second solvent being substantially immiscible in said first solvent, wherein said keratin is substantially insoluble in said second solvent;

providing an oxidizing agent;

emulsifying said keratin solution and said second solvent together;

freezing said emulsion;

removing at least a substantial portion of said first and second solvents under vacuum and low temperature, such that a porous keratin material is created; and warming said porous keratin material in the presence of said oxidizing agent, such that said porous keratin free thiol groups are oxidized to form disulfide cross-links and cross-link the porous keratin material.

6. A method for making a porous, cross-linked keratin material comprising the steps of:

providing a keratin solution including keratin in solution in a first solvent, said keratin having free thiol groups;

providing an oxidizing agent;

atomizing said keratin solution;

spraying said atomized keratin solution onto a cold surface such that said atomized keratin is frozen;

spraying more of said atomized keratin onto said frozen atomized keratin such that a layer of frozen atomized keratin is created;

removing a substantial portion of said first solvent under vacuum and low temperature, such that a porous keratin material is created; and warming said porous keratin material in the presence of said oxidizing agent, such that said porous keratin free thiol groups are oxidized to form disulfide cross-links and cross-link said porous keratin material.

7. A method as recited in claim 6, wherein said cold surface is the inside surface of a mold.

8. A method for making porous keratin material comprising the steps of: providing vertebrate hair having disulfide linkages;

reducing said hair, such that some of said disulfide linkages are broken and a more soluble keratin fraction and a less soluble keratin fraction are formed;

collecting said more soluble keratin fraction;

providing said collected more soluble keratin fraction in a solvent;

removing some of said solvent from said soluble keratin fraction layer;

depositing said soluble keratin fraction into an open-cell material;

removing more of said solvent from said soluble keratin fraction in said open-cell material; and oxidizing said keratin in said open-cell material with an oxidizing agent.

9. A method as recited in claim 8, wherein said solvent removing step includes drying in the presence of gaseous oxygen and wherein said oxidizing agent includes said oxygen.

10. A method as recited in claim 8, wherein said solvent removal step includes air drying and said oxidizing agent includes air.

11. A method as recited in claim 8, wherein said solvent removing step includes removing said solvent under sub-ambient pressure.

12. A method as recited in claim 8, wherein said oxidizing agent includes hydrogen peroxide.

13. A method as recited in claim 8, further comprising comminuting said hair into smaller pieces prior to said collecting step.

14. A method as recited in claim 13, wherein said comminuting includes homogenizing said hair.

15. A method as recited in claim 8, wherein said reducing step includes heating said hair in the presence of thioglycolic acid.

16. A method as recited in claim 8, wherein said reducing step includes heating said hair in a basic solution including ammonium hydroxide and ammonium thioglycolate.

17. A method for making a keratin based porous material comprising the steps of:

providing keratin containing material having disulfide linkages;

providing an oxidizing agent;

providing a solvent;

suspending said keratin containing material in a basic solution of ammonium hydroxide and ammonium thioglycolate;

comminuting said keratin containing material in said solution into smaller pieces;

heating said solution;

reducing said keratin containing material, such that some of said disulfide linkages are broken and a slurry is formed including a more soluble keratin fraction and a less soluble keratin fraction;

collecting said more soluble keratin fraction;

concentrating said collected keratin fraction;

emulsifying said concentrated keratin fraction together with said solvent;

freeze drying said emulsion, such that a frozen, porous keratin material is formed; and warming said frozen porous keratin material in the presence of said oxidizing agent such that said keratin forms disulfide cross-links.

18. A porous keratin material resulting from the process comprising the steps of:

providing cut, washed, and dried hair, wherein said hair includes keratin having disulfide linkages;

providing a non-polar solvent;

providing a gas including gaseous oxygen;

suspending said hair in a solution of about 3N ammonium hydroxide and ammonium thioglycolate, wherein said hair is added in an amount of about 6 grams per 75 mL of ammonium hydroxide and said ammonium thioglycolate is added in an amount of about 11 mL of thioglycolic acid per 75 mL of ammonium hydroxide;

heating said hair suspension at about 60° Centigrade for about 2 hours under a nitrogen atmosphere;

homogenizing said hair suspension with a tissue homogenizer for about 30 minutes such that a fine dispersion is formed;

further heating said homogenized hair suspension under nitrogen at about 60° Centigrade for about 2 hours;

cooling said hair suspension to room temperature;

centrifuging said hair suspension at about 10,000 g for about 10 minutes such that a supernatant containing a more soluble keratin fraction is formed;

collecting said supernatant and treating said supernatant with HCl until a keratin fraction precipitates out;

collecting said precipitate;

washing said precipitate with deionized water;

dissolving said precipitate in 3N ammonium hydroxide such that a keratin solution is formed;

concentrating said keratin solution;

emulsifying said concentrated keratin solution in said non-polar solvent;

freeze drying said concentrated, emulsified keratin solution; and warming said freeze dried keratin in the presence of said gas, such that a porous keratin material piece is formed.

19. A porous keratin material resulting from the process comprising the steps of:

providing hair, wherein said hair includes keratin having disulfide linkages;

reducing said hair with a reducing agent, such that a significant percentage of said disulfide linkages are reduced to cysteine thiol groups;

separating said reduced hair into a more soluble in-water aqueous keratin fraction and a less soluble in-water keratin fraction;

removing some of said water from said more soluble keratin fraction;

freeze drying said more soluble keratin fraction; and oxidizing said more soluble keratin fraction with an oxidizing agent, such that a significant percentage of said reduced cysteine thiol groups are oxidized to form new disulfide linkages, such that a keratin containing material having said new disulfide linkages is formed within an open-cell material.

20. A method for making keratin based porous material comprising the steps of:

providing keratin containing material having disulfide linkages;

providing a solvent;

reducing said keratin containing material, such that said disulfide linkages are broken and a more soluble keratin fraction and a less soluble keratin fraction are formed;

separating said more soluble keratin fraction from said less soluble keratin fraction;

collecting said more soluble keratin fraction;

concentrating said more soluble keratin fraction;

emulsifying said concentrated more soluble keratin fraction together with said solvent;

freeze drying said emulsion; and warming said emulsion in the presence of oxygen.

* * * * *